United States Patent
Hubinette

(10) Patent No.: US 10,799,451 B2
(45) Date of Patent: Oct. 13, 2020

(54) NICOTINE FORMULATION

(71) Applicant: NICOCCINO AB, Taby (SE)

(72) Inventor: Fredrik Hubinette, Uppsala (SE)

(73) Assignee: NICOCCINO AB, Taby (SE)

(*) Notice: Subject to any disclaimer, the term of this patent is extended or adjusted under 35 U.S.C. 154(b) by 25 days.

(21) Appl. No.: 16/197,954

(22) Filed: Nov. 21, 2018

(65) Prior Publication Data

US 2019/0091135 A1 Mar. 28, 2019

Related U.S. Application Data

(63) Continuation-in-part of application No. 14/386,083, filed as application No. PCT/EP2013/055456 on Mar. 15, 2013, now abandoned.

(Continued)

(30) Foreign Application Priority Data

Mar. 27, 2012 (EP) ..................... 12161483

(51) Int. Cl.
   *A61K 9/00* (2006.01)
   *A61K 31/465* (2006.01)
   (Continued)

(52) U.S. Cl.
   CPC ............ *A61K 9/006* (2013.01); *A61K 9/7007* (2013.01); *A61K 31/465* (2013.01); *A61K 47/02* (2013.01);
   (Continued)

(58) Field of Classification Search
   None
   See application file for complete search history.

(56) References Cited

U.S. PATENT DOCUMENTS

| 5,298,257 A | 3/1994 | Bannon et al. |
| 5,362,496 A | 11/1994 | Baker et al. |

(Continued)

FOREIGN PATENT DOCUMENTS

| WO | 2007/073346 | 6/2007 |
| WO | 2009/074552 | 6/2009 |
| WO | 2010/104464 | 9/2010 |

OTHER PUBLICATIONS

International Search Report dated Apr. 22, 2013, corresponding to PCT/EP2013/055456.

(Continued)

*Primary Examiner* — Dennis R Cordray
(74) *Attorney, Agent, or Firm* — Nixon & Vanderhye

(57) ABSTRACT

A method of manufacturing a nicotine-containing mucoadhesive film, by preparing an aqueous solution at a pH of from 9.5 to 13, the solution includes (i) a nicotine salt, (ii) an alkaline pH-regulating agent, and (iii) a film-forming agent including an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2; distributing the solution onto a solid surface; and permitting the solution to dry on said surface. A nicotine-containing mucoadhesive film.

20 Claims, 1 Drawing Sheet

Related U.S. Application Data

(60) Provisional application No. 61/615,997, filed on Mar. 27, 2012.

(51) Int. Cl.
  *A61K 47/36* (2006.01)
  *A61K 47/02* (2006.01)
  *A61K 9/70* (2006.01)
  *A61K 47/26* (2006.01)
  *A61K 47/10* (2017.01)

(52) U.S. Cl.
  CPC .............. *A61K 47/10* (2013.01); *A61K 47/26* (2013.01); *A61K 47/36* (2013.01)

(56) References Cited

U.S. PATENT DOCUMENTS

| | | |
|---|---|---|
| 5,824,334 A | 10/1998 | Stanley et al. |
| 6,790,496 B1 | 9/2004 | Levander |
| 2006/0198873 A1* | 9/2006 | Chan .................... A61P 25/00 424/443 |
| 2008/0286340 A1 | 11/2008 | Andersson |
| 2009/0221489 A1 | 9/2009 | Stenberg et al. |

OTHER PUBLICATIONS

European Search Report dated Jul. 2, 2012, corresponding to the Foreign Priority Application No. EP 12 16 1483.

T. Pongjanyakul, et al.; "Nicotine-Loaded Sodium Alginate-Magnesium Aluminum Silicate (SA-MAS) Films: Importance of SA-MAS Ratio"; vol. 80, No. 4; May 1, 2010; pp. 1018-1027.

Kanjanabat Sopaphan, et al.; "Preparation and Characterization of Nicotinea Magnesium Aluminum Silicate Complex-Loaded Sodium Alginate Matrix Tablets for Buccal Delivery"; vol. 12, No. 2; May 19, 2011; pp. 683-692.

T. Pongjanyakul, et al.; "Alginate-Magnesium Aluminum Silicate Films for Buccal Delivery of Nicotine"; vol. 74, No. 1; Nov. 1, 2009; pp. 103-113.

* cited by examiner

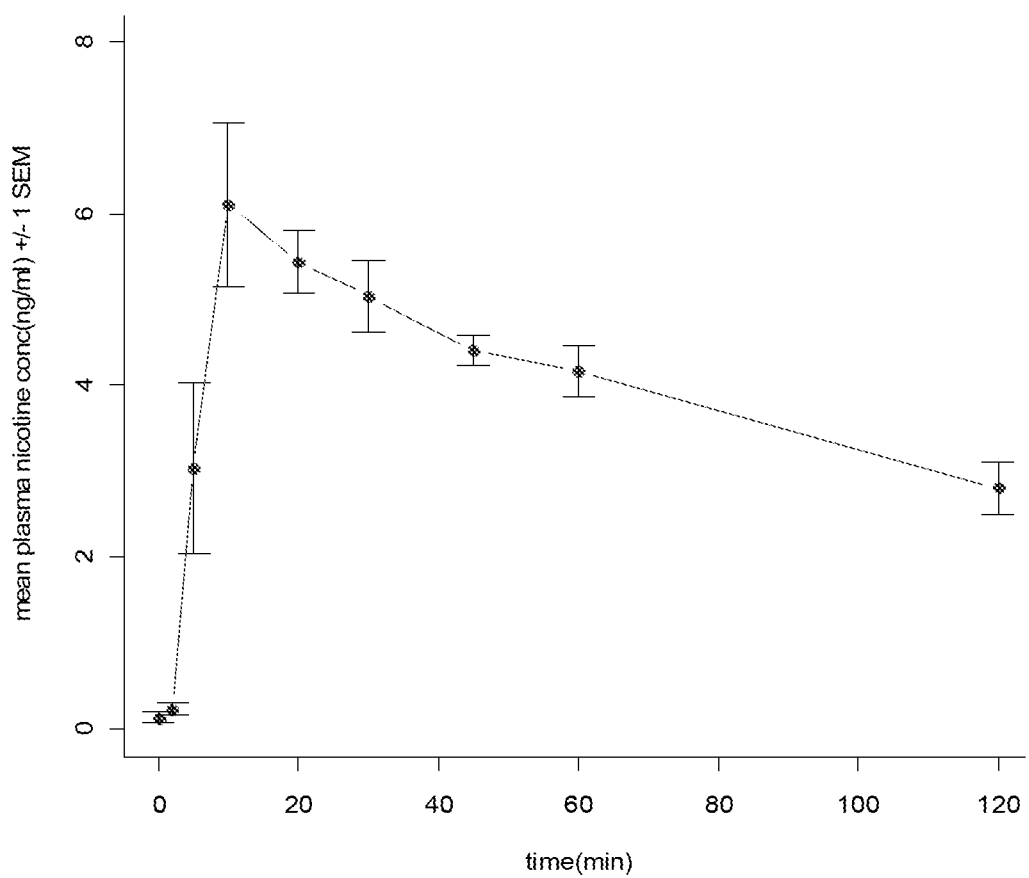

NICOTINE FORMULATION

FIELD OF THE INVENTION

The present invention relates to a nicotine film formulation for administration of nicotine to a human subject and to a method for preparing such formulation.

BACKGROUND OF THE INVENTION

A well-known therapeutic approach to aid in smoking cessation is to provide the smoker with nicotine from sources other than cigarettes. For example, there are a number of commercially available nicotine replacement products that deliver nicotine to the systemic circulation via absorption through mucosal membranes or through the skin. These include e.g. nicotine-containing chewing gums and lozenges, as well as transdermal patches.

Both the nicotine lozenge and the nicotine chewing gum contain nicotine bitartrate or nicotine resinate. On chewing the gum or sucking the lozenge, the nicotine salt is released from the gum or lozenge and absorbed through the lining of the mouth. However, some of the nicotine also will be swallowed together with the saliva, which will reduce the amount entering the systemic circulation directly without passing through the gastric system. Another disadvantage of the lozenge or chewing gum is that the required chewing or sucking must be performed for some time in order for the entire dose to be released, which in some circumstances may be awkward or socially unacceptable. There are other evident disadvantages of these forms of administration, e.g. the taste which is not always perceived as agreeable, the litter resulting from the chewed chewing gum and even the suggested possibility that the resin of the chewing gum may lead to cancer in the mouth or throat.

By the above-mentioned nicotine delivery devices absorption occurs quite slowly and provides a low, steady-state blood level of nicotine to the patient without the early nicotine concentration spike that occurs due to immediate, arterial delivery of nicotine to the brain obtained when smoking a cigarette. In fact, a goal of these therapies is to eliminate the immediate, pleasurable effects associated with smoking while still alleviating the nicotine withdrawal effects until complete cessation of nicotine is physically and psychologically possible for the patient. However, this complete lack of "rush effect" experienced by the patient, may in part explain the rather low success rates of these conventional therapies, as discussed in e.g. U.S. Pat. No. 5,298,257 to Bannon et al.

Nicotine, or 3-[(2S)-1-methylpyrrolidin-2-yl]pyridine, is a hygroscopic, water-miscible, oily liquid alkaloid containing two basic nitrogen-containing rings, the pyrrolidine ring and the pyridine ring.

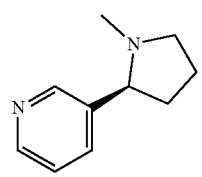

3-[(2S)-1-methylpyrrolidin-2-yl]pyridine

The pyrrolidine nitrogen is more basic than the pyridine nitrogen and, thus, nicotine may be dipronotated, monopronotated or free base (i.e. unprotonated).

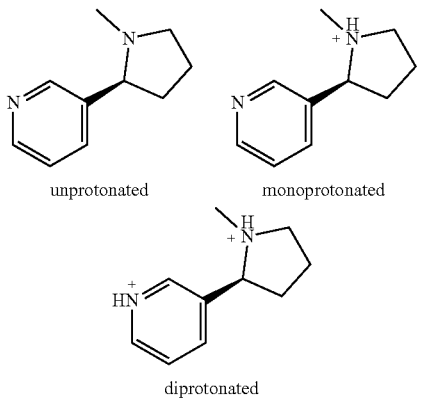

unprotonated     monoprotonated diprotonated

It is well-known that it is the free base nicotine, present in the cigarette smoke, that is behind the more rapid rush effect. However, in free base form, nicotine evaporates even at a temperature as low as room temperature. Furthermore, as a free base, it also is easily degraded by oxygen and light.

Free base nicotine also is very aggressive towards its environment and migrates through most known materials. Furthermore, free base nicotine, being very hygroscopic, is very sensitive to moisture. Finally, when exposed to oxygen or air free base nicotine turns brown. These stability and migration problems inherent to the free base nicotine molecule are discussed in U.S. Pat. No. 6,790,496, which suggests a solution to this problem based on packaging of the nicotine-containing products in special packing materials.

To the knowledge of the inventors, presently, the only commercially available, non-tobacco containing products offering a rush effect similar to that obtained when smoking a cigarette are aerosol devices of the type sold under the trade mark NICORETTE® QuickMist. However, the use of nicotine spray is not without drawbacks. For example, nicotine spray users have reported discomforts such as tingling lips, hiccups and disagreeable taste of the aerosol product. Other drawbacks are e.g. the inherent risk of loss to the surrounding air when using the spray, and the environmentally detrimental need for packaging material in the spray canisters.

From the above it appears that there still is a need for a smoking cessation product that at the same time is capable of releasing free base nicotine in a way that more or less emulates cigarettes, and still is stable against evaporation or degradation of the nicotine.

SUMMARY OF THE INVENTION

It is an object of the present invention to provide a product for nicotine delivery that essentially solves the above-mentioned problems of the prior art nicotine delivery products.

One important object of the present invention is to provide a nicotine formulation capable of keeping its nicotine content during storage, yet being able to deliver nicotine free base when administered to a human subject.

Thus, according to a first aspect a nicotine containing mucoadhesive film is provided, obtainable by
preparing an aqueous solution at a pH of from 9.5 to 13, said solution comprising
(i) a nicotine salt,
(ii) an alkaline pH-regulating agent, and
(iii) a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;

distributing the solution onto a solid surface; and permitting the solution to dry on said surface.

According to another aspect, there is provided a method of manufacturing a nicotine-containing mucoadhesive film, comprising:

preparing an aqueous solution at a pH of from 9.5 to 13, said solution comprising
(i) a nicotine salt,
(ii) an alkaline pH-regulating agent, and
(iii) a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;

distributing the solution onto a solid surface; and permitting the solution to dry on said surface.

The film of the invention is useful for buccal transmucosal delivery of nicotine.

Some advantages of the methods and formulations of the present invention are that:

pH buffering systems can be omitted from the formulation of the invention;

high systemic uptake of nicotine free base is obtained through the oral mucosa;

the dry formulation contains only very small amounts of free base nicotine available to reactions induced by air and light, keeping the product stable over time; and nicotine is incorporated in the formulation in the form of water soluble salt, and as such is easy to distribute evenly throughout a solution, thereby providing a homogeneous distribution of nicotine in the formulation.

The nicotine film of the present invention suitably is a stand-alone, one layer film.

BRIEF DESCRIPTION OF THE DRAWING

FIG. 1 is a graph showing nicotine concentration (mean+/−SEM), in ng/ml, in blood samples collected from 5 healthy subjects over a 2-hour period after administration of a film dosage unit according to the invention containing 2 mg of nicotine (in the form of nicotine salt).

DETAILED DESCRIPTION OF THE INVENTION

The nicotine film of the present invention is obtainable by:

preparing an aqueous solution at a pH of from 9.5 to 13, said solution comprising
(i) a nicotine salt,
(ii) an alkaline pH-regulating agent, and
(iii) a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;

distributing the solution onto a solid surface; and permitting the solution to dry on said surface.

The nicotine salt may be any pharmaceutically acceptable nicotine salt. Nicotine is able to form salts with many metals and acids. The acids that may be used to prepare the pharmaceutically acceptable acid salts of nicotine are those that form non-toxic acid salts, i.e., salts containing pharmaceutically acceptable anions, such as hydrochloride, hydrobromide, hydroiodide, nitrate, sulphate or bisulphate, succinate, maleate, fumarate, bitartrate, gluconate, saccharate, benzoate, methanesulphonate, ethanesulphonate, benzenesulphonate, p-toluene sulphonate, camphorate and pamoate salts. Particularly preferred are the tartrate and bitartrate salts.

Preferably, the alkaline pH regulating agent is a strong base, such as LiOH, NaOH or KOH. In one embodiment, the alkaline pH regulating is NaOH.

The nicotine formulation of the invention additionally may comprise any suitable excipient, such as one or more fillers or plasticizers. An example of a filler e.g. is microcrystalline cellulose. The plasticizer, when present, may be selected from e.g. polyethylene glycols, glycerol and sorbitol.

Optionally, the nicotine formulation of the invention also may comprise any physiologically (e.g. non-toxic at the added level) and/or pharmacologically acceptable additive, such as one or more flavouring agents (taste maskers) and/or colouring agents. Examples of flavouring agents are sorbitol, peppermint, orange flavouring, lemon flavouring, cherry flavouring, and cranberry extract. Examples of colouring agents are titanium dioxide and green or red food colour.

The film-forming agent of the present invention is an alginate salt of a monovalent cation or a mixture of alginate salts of monovalent cations, the film-forming agent having a mean guluronate (G) content of from 50% to 85% by weight, a mean mannuronate (M) content of from 15% to 50% by weight, a mean molecular weight of from 30,000 g/mol to 90,000 g/mol and being such that an aqueous solution of 10% thereof at a temperature of 20° C. has a viscosity of 100 mPas to 1000 mPas, as measured at a shear rate of 20 rpm by use of a Brookfield viscometer with a spindle No. 2. Such a film-forming agent is described in patent application PCT/SE2006/050626 (WO 2007/073346) the disclosure of which is incorporated herein by reference.

Thus, the nicotine formulation of the invention is a water-soluble film, such as a mucoadhesive film, which on application to oral mucosa adheres thereto and dissolves, allowing active ingredients contained in the film to penetrate the mucosal membrane and enter the blood stream. Such a mucoadhesive film is generally described in PCT/SE2006/050626 (WO 2007/073346).

In some embodiments of a nicotine film formulation, sorbitol and/or glycerol are used as plasticizers. A suitable amount of plasticizer is e.g. from 10 to 85 g, or from 30 to 70 g, e.g. from 50 to 60 g of plasticizer per 100 g of film-forming agent, e.g. alginate.

In some embodiments of the nicotine film formulation, filler(s) are present in an amount of 0-20%, e.g. 5-10% by weight of the total pharmaceutical composition.

The nicotine formulation according to the present invention is a dry formulation, and is prepared by a method comprising a drying step. By "dry" is meant that the formulation may at most have a humidity corresponding to equilibrium with a surrounding atmosphere having a relative humidity of from 10 to 40%, e.g. from 20 to 30%, at 25° C.

In one embodiment of the invention, the alkaline nicotine-containing film-forming solution (the "casting solution") is obtained by:

preparing an aqueous solution of a nicotine salt, and an alkaline pH regulating agent providing an alkaline pH in the aqueous solution; and admixing said aqueous solution with a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2, so as to obtain an aqueous solution containing the film forming agent and the nicotine salt, said solution having a pH of from 9.5 to 13.

In this embodiment, the alkaline pH regulating agent may be added to the aqueous nicotine salt solution in an amount providing a pH of at least 10, or at least 11, at least 11.5, at least 12, at least 12.4, or at least 12.5, e.g. a pH in the range of from 10 to 13, or from 11 to 13, such as from 11.5 to 13, e.g. from 12 to 13, or from 12.4 to 12.8, e.g. from 12.5 to 12.7.

In particular, the alkaline pH regulating agent is added to the aqueous nicotine salt solution in an amount such that after admixing the alkaline nicotine-containing solution (optionally containing also other ingredients, such as flavor, plasticizer, filler etc.) with the alginate salt, a casting solution is obtained having a pH of at least 9.5, at least 9.7, at least 10, at least 10.5, at least 10.7, at least 11, or at least 11.5. For example, the $pH_{ii}$ may be from 9.5 to 12.5, or from 9.7 to 12.2, or from 10 to 11.7, such as from 10.5 to 11.5, e.g. from 10.7 to 11.5, or from 11 to 11.5, e.g. from 11.2 to 11.5.

For example, in one embodiment, a nicotine salt such as nicotine bitartrate is mixed with water and e.g. a suitable metal ion hydroxide salt, such as NaOH, as a basifying agent, so as to provide an aqueous nicotine solution having a pH as indicated herein above, e.g. in the range of from 10 to 13, or from 11 to 13, such as from 11.5 to 13, e.g. from 12 to 13, or from 12.4 to 12.8, e.g. from 12.5 to 12.7. In light of the present disclosure and by consulting also the Examples herein, the person of ordinary skill in the art will be well enabled to find the specific p, necessary in order to obtain the selected pH of at least 9.5 for the casting solution.

Optional ingredients, such as flavor, plasticizer, filler, may be added at any moment, e.g. after adding the basifying agent, but preferably should be added before admixing of the alginate. Next, the film-forming alginate is admixed with the aqueous nicotine solution and the mixture may then be poured into suitable casting dies or onto a solid casting surface and allowed to dry.

In one embodiment, the method for preparing the mucoadhesive nicotine-containing film of the invention comprises:

(i) preparing an aqueous solution of a nicotine salt and an alkaline pH-regulating agent, said solution having a $pH_i$ which is higher than $pH_{ii}$;

(ii) adding, to the solution obtained in (i), a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2; so as to obtain an aqueous solution containing the film forming agent and the nicotine salt, said solution having a $pH_{ii}$ of from 9.5 to 13;

(iii) distributing the solution onto a solid surface; and (iv) permitting the solution to dry on said surface.

In another embodiment, the method for preparing the mucoadhesive nicotine-containing film of the invention comprises (i) preparing separately:

(a) an aqueous solution of a film-forming agent comprising an alginate salt of monovalent cation or a mixture of alginate salts of monovalent cations, the film-forming agent having a mean guluronate (G) content of from 50 to 85% by weight, a mean mannuronate (M) content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2; and (b) an aqueous solution of a nicotine salt;

whereby at least one of the two solutions (a) and (b) contains an alkaline pH regulating agent;

(ii) admixing the two solutions so as to obtain a nicotine-containing film-forming solution having a pH of from 9.5 to 13;

(iii) distributing the solution onto a solid surface; and (iv) permitting the solution to dry on said surface.

In one embodiment, solution (a) contains an alkaline pH regulating agent.

In one embodiment, solution (b) contains an alkaline pH regulating agent.

Drying preferably is effected until the formulation reaches a level of dryness equal to that which it would have in equilibrium with a surrounding atmosphere having a relative humidity of 10 to 40% at 25° C., e.g. 20 to 30% at 25° C., e.g. a water content of about 8% by weight.

To prepare a dry film, the process for preparing a dry film as generally described in WO 2007/073346 may be followed.

For example, the casting solution is distributed onto a solid, flat surface as a wet film having a thickness of from e.g. 0.1 to 4 mm, such as 0.2 to 2 mm, e.g. 0.5 to 1.5 mm. The wet film then is allowed to dry on the surface, e.g. in room temperature or in a ventilated oven or drying cabinet at a temperature of 45-60° C., e.g. at a temperature of from 52 to 54° C., for a time period of e.g. 20 to 40 minutes, or from 20 to 30 minutes.

After drying at least partly of the film, the dry or semi-dry film thus obtained may be divided into suitably sized dosage units, e.g. by cutting or punching.

The film may be imprinted imprinted at one or both sides with words, figures or other markings, e.g. a trade mark or an indicating of the dosage, using an ink suitable for human ingestion. For example a 2 mg dosage unit may be imprinted with "2 mg".

The dry dosage units may be packaged into suitable containers, e.g. resealable containers of a water and air tight material suitable for use in packaging of products for human ingestion, e.g. a metallised polyethylene film (Alu/PET).

As illustrated in the stability test described herein below, by the method of the present invention, a nicotine film formulation having a high shelf life is obtained. It is remarkable that the nicotine content of the film remains essentially unchanged over a time period of nearly four months without any precautions being taken to preserve the film from either light or surrounding air.

When administered to the mouth of a human subject, the formulation will dissolve by the action of the saliva, releasing the basifying pH regulating agent and nicotine free base. As the nicotine free base penetrates the oral lining and enters the blood stream, the desired rush effect may be obtained.

It is an advantageous feature of the nicotine formulation of the present invention that it is in the form of a mucoadhesive film. When applied to the mucous membrane of the mouth, the dry film will adhere thereto and dissolve over a given time period, e.g. 1 minute to 10 minutes, such as 1-5 minutes, or 1-3 minutes. As the film dissolves, the nicotinic salt and the basifying agent are released. The basifying agent will provide a high local pH in the liquid phase formed by the saliva at the oral mucosa in contact with the dissolving mucoadhesive film. In this high pH liquid solution nicotine will be present again as a free base, and as such will penetrate the mucous membrane and enter the blood stream of the body. Systemic parenteral delivery of free base nicotine thereby is obtained.

The dry film formulation according to the invention preferably has a thickness of 0.01 to 2 mm, or 0.02 to 1 mm, e.g. 0.05 to 0.5 mm, or from 0.06 to 0.4 mm, or from 0.06 to 0.1 mm, e.g. about 0.07 mm.

In one embodiment, the nicotine-containing film of the invention is provided in dosage units. Such dosage unit may be of any suitable surface area, having regard to the concentration of the nicotine salt within the film and the suitable nicotine dosage to be administered. As an example, a dosage unit having a surface area of from 1 $cm^2$ to 10 $cm^2$ may be selected, e.g. from 2 to 8 $cm^2$, or from 4 to 7 $cm^2$, such as about 6 $cm^2$. It will be within the knowledge of the skilled person to adapt the size and shape of the film dosage unit having regard to such parameters as e.g. the loading of the nicotine salt within the film and the required dosage. Also, it should be realized that the film dosage unit may have any appropriate shape, e.g. it may be rectangular, circular, oblong, oval etc.

A suitable dosage unit e.g. may be contain from 0.5 mg to 4 mg nicotine in the form of nicotine salt, e.g. from 1 to 2 mg nicotine, or any other suitable amount. For example, a dosage unit may be a dry film unit having a surface area of 3 $cm^2$, a thickness of about 0.2 mm and containing about 2 mg nicotine. In one embodiment, the dosage unit is a dry film unit having a surface area of 6 $cm^2$, a thickness of about 0.07 mm, containing about 2 mg nicotine. In another embodiment, the dosage unit is a dry film unit having a surface area of 6 $cm^2$, a thickness of about 0.07 mm, containing about 1 mg nicotine.

An important advantageous feature of the nicotine film of the present invention is its capacity of providing a high systemic availability due to the transmucosal absorption of nicotine. Compared to nicotine chewing gums, where a large part of the nicotine is swallowed down with the saliva, this will allow for a reduced dosage of nicotine.

A further advantage provided by the nicotine film of the invention is the very simple, easy to handle dosage form, compared e.g. to the aerosol spray.

Another advantageous feature of the nicotine film of the invention is storage stability of the nicotine in the film, which may allow for a multi-dosage package of dosage units of the film without any need for individual packaging of each dosage unit. Thus, in one embodiment, a resealable package is provided containing a plurality of nicotine-containing film dosage units according to the invention. For example, such a resealable package may contain from 5 to 200 dosage units, or from 10 to 100 dosage units, e.g. from 20 to 50 dosage units, such as 30 dosage units.

In some embodiments, each dosage unit is packaged separately in an air and water tight material, such as a metallised polymeric film, e.g. an Alu/PET film. For example, each dosage unit may be provided separately in an Alu/PET envelope.

Herein below, the invention will be illustrated by the following non-limiting examples.

EXAMPLES

Example 1

A mucoadhesive nicotine-containing film according to the invention was prepared using the ingredients listed in Table 1.

TABLE 1

| Ingredient | Amount |
| --- | --- |
| nicotine tartrate | 3.7 g |
| water | 174.5 ml |
| sorbitol | 6 g |
| glycerol | 6 g |
| NaOH 2M | 20.5 ml |
| titanium dioxide | 0.3 g |
| lemon flavour | 2 ml |
| peppermint flavour | 1 ml |
| sodium alginate (Protanal ®LFR 5/60, sold by FMC BioPolymer) | 26.7 g |

The film was prepared as follows: In a beaker, water was mixed with nicotine tartrate and NaOH until a clear solution was obtained. The pH was adjusted to within a range of from 11.8 to 12.8. Titanium dioxide was added and the solution was sonicated to provide a homogenous dispersion of titanium dioxide in the nicotine solution. Next, ⅓ of the alginate was added and the solution was mixed in a mixer so as to obtain a visibly homogeneous liquid phase. While maintaining the stirring, glycerol, sorbitol and the flavouring agents were added. The remainder of the alginate then was added and the mixing was continued until obtaining a homogenous, viscous liquid phase. The liquid mixture then was transferred to a glass beaker and sonicated again to remove any air bubbles therein. Subsequently, ¼ of the liquid mixture was distributed homogeneously over a glass plate at a thickness of 0.89 mm by means of a draw down blade for wet film application. The film was dried in a drying cabinet at a temperature of 45 to 60° C. for 25 minutes. The dry film was cut into rectangular pieces of 2×3 $cm^2$ and the samples of nicotine film were placed in clean, plastic pockets.

A stability study of nicotine in the film of the invention was performed in order to establish the shelf life of nicotine in an opened multi-dose package. The dosage units prepared in EXAMPLE 1 were used in the test. At day 0 of the study, the plastic pocket containing the dry film samples was opened and the nicotine concentration in 3 dosage units (i.e. three 6 cm² pieces) of the film formulation was determined. The remaining dosage units contained in the plastic pocket were stored in the open at a temperature ranging from 21 to 24° C. and a relative humidity of 19-32%. These film dosage units were not stored in the dark, but simply kept in the open, on a shelf in the laboratory. The nicotine concentration of 3 different dosage units was measured again at day 7 and at day 102, respectively. The results are listed in Table 2 herein below.

TABLE 2

| Days after opening of package | Nicotine mg/dosage unit |
|---|---|
| 0 | 1.328 |
| 7 | 1.328 |
| 102 | 1.310 |

Overview of Method and Equipment for Analysis

Analysis was performed using the following equipment:

Isocratic HPLC-pump: Constametric Model III

Auto injector: Dynamax Model AI3 (Loop volume 50 µl)

Column heater: Jones Chromatography Model 7981 (Temperature 35° C.)

Column: Dr Maisch, Reprosil-Pur Basic, C18-AQ 5 µm, 150×4 mm

UV-detector: PerSeptive Biosystems UVIS-205 (at 260 nm)

Flow rate 1 ml/min

Mobile phase: 30% ACN, 70% 10 mM Phosphate Buffer pH 8.5

Diluent 15% ACN, 85% 10 mM Phosphate Buffer pH 8.5

A standard curve using nicotine bitartrate dihydrate in diluent was used. The samples where diluted in 100 ml of diluent and filtrated through a 0.4 µm filter.

Example 2

A mucoadhesive nicotine-containing film according to the invention was prepared essentially as described in EXAMPLE 1, using the ingredients listed in Table 3.

TABLE 3

| Ingredient | Amount |
|---|---|
| nicotine tartrate | 5.1 g |
| water | 171 ml |
| sorbitol | 7 g |
| glycerol | 7 g |
| NaOH 2M | 24 ml |
| titanium dioxide | 0.3 g |
| lemon flavour | 2 ml |
| peppermint flavour | 1 ml |
| sodium alginate (Protanal ®LFR 5/60, sold by FMC BioPolymer) | 26.7 g |

Dosage units containing 2 mg nicotine/unit were prepared. The systemic delivery of nicotine by peroral administration of these dosage units was assessed on 5 healthy subjects.

Before administration of the dosage unit, a blood sample was withdrawn from the subject to establish a zero level. At that point of time, the subjects had not used any nicotine-containing product for at least 24 hours.

At time zero, a film dosage unit of the invention was applied to the palate of each subject. Blood samples were collected from each subject at regular intervals during 2 hours. Plasma was separated, frozen using dry ice and sent to a GLP accredited laboratory for analysis. The analytical method was developed at the laboratory and validated according to the FDA Guidance for Industry—Bioanalytical Method Validation (CDER, May 2001). The tabulated summary of this validation is shown in Table 4.

TABLE 4

Validation summary for the quantification of nicotine in human plasma by LC-MS/MS

| Analyte | Nicotine |
|---|---|
| Internal standard | Nicotine-d4 |
| Matrix (Anticoagulant) | Human Plasma (Lithium Heparin) |
| SOP Number | 5-85 |
| Analytical Method | High performance liquid chromatography (HPLC) coupled to tandem mass spectrometry with multiple reaction monitoring (MRM) |
| Detector | AB/MDS Sciex API 4000 |
| Human Plasma Volume Required | 100 µL |
| Standard Curve Range | 0.5-100 ng/mL |
| QC concentrations | 1.5, 15, 80 ng/mL |
| Regression Type | Linear regression (weighted 1/concentration 2) |
| Quantification Method | Peak area ratio |
| Selectivity | No interfering peaks noted in blank plasma samples |

| LLOQ Validation Samples | Precision (%) | Bias (%) |
|---|---|---|
| Inter-batch | 7.9% | −4.2% |
| Intra-batch | 4.05% to 6.81% | −0.91% to 12.66% |

| Quality Control Samples | Precision (%) | Bias (%) |
|---|---|---|
| Inter-batch Low | 7.3% | 2.3% |
| Inter-batch Medium | 2.0% | 2.9% |
| Inter-batch High | 2.4% | 5.6% |
| Intra-batch Low | 3.19% to 3.55% | −6.96% to 7.03% |
| Intra-batch Medium | 0.96% to 2.52% | 1.39% to 3.91% |
| Intra-batch High | 1.83% to 2.50% | 3.84% to 6.68% |

TABLE 4-continued

Validation summary for the quantification
of nicotine in human plasma by LC-MS/MS

| Recovery | Recovery (%) |
|---|---|
| Analyte Low | 99% |
| Analyte Medium | 134% |
| Analyte High | 78% |
| Internal Standard | 90% |
| Long-term Stability | 103 days at −20° C. |
| Short-term Stability | 24 hours at room temperature and 120 hours at 4° C. |
| Freeze - Thaw Stability | 4 cycles at −20° C. |
| Stock Solution Stability | 29 days in acidified water at 4° C. |
| Processed Sample Stability | 72 hours at 4° C. and room temperature |

Samples of human plasma with an added internal standard were extracted using a liquid-liquid extraction procedure. After evaporation and resuspension in LC mobile phase, the samples were analyzed by LC-MS/MS. Positive ions were monitored in the multiple reaction monitoring (MRM) mode. Quantification was by peak area ratio.

The results, in terms of plasma nicotine concentration (in ng/ml) in the blood plasma samples, are illustrated in FIG. 1. The indicated values are mean values calculated from the 5 subjects participating in the test.

Example 3

The ingredients used in the Example are indicated in Table 5.

TABLE 5

| Ingredient | Amount |
|---|---|
| nicotine bitartrate | 5.1 g |
| sorbitol | 7 g |
| glycerol | 7 g |
| NaOH 2M | enough to $pH_i$ ($V_1$ ml) |
| water | enough to 195 ml with $V_1$ and $V_2$ |
| titanium dioxide | 0.3 g |
| lemon flavour | 2 ml |
| peppermint flavour | 1 ml |
| sodium alginate (Protanal ®LFR 5/60, sold by FMC BioPolymer) | 26.7 g |

An aqueous nicotine bitartrate solution of 5.1 g nicotine bitartrate in about 160 ml of water was prepared and 2 M NaOH was added until an alkaline pH was reached ($pH_i$). Titanium dioxide, dissolved in a small amount of water ($V_2$ ml), was added. The total volume of the aqueous alkaline solution was adjusted to 195 ml by addition of further water. Sorbitol, glycerol, and flavours were added to the alkaline solution, followed by the sodium alginate. The pH was measured ($pH_{ii}$) on a sample diluted 1:2. The solution then was cast and dried to provide a dry film. From the dry film 6 cm², 0.07 mm thick samples weighing 70 mg were cut and dissolved in 10 ml of water, and the pH of the aqueous solution was measured.

The nicotine contents of film samples were measured directly after drying and after 30 days storage at 25° C., ambient RH, packed in Alu/PET pouches. The results are shown in Table 6.

TABLE 6

| $pH_i$ in nicotine solution before addition of alginate | $pH_{ii}$ in wet cast (50/50 $H_2O$) | pH dried film in $H_2O$ (10 mL) | nicotine content drop from initial value (%) |
|---|---|---|---|
| 10.7 | 8.8 | 8.47 | >5% |
| 12.22 | 9.24 | 8.81 | >5% |
| 12.37 | 9.5 | 9.04 | <5% |
| 12.52 | 11.18 | 9.82 | <5% |
| 12.88 | 12.3 | 10.41 | <5% |

From the results in Table 6, it surprisingly appears that a nicotine containing film prepared by use of a film-forming solution of the invention, having a pH of at least 9.5, has a good stability, whereas when the pH of the film-forming solution is lower than about 9.5, the stability of the nicotine in the dry film is insufficient.

Example 4

The ingredients used in Example 4 are listed in Table 7.

TABLE 7

| Ingredient | Amount |
|---|---|
| nicotine bitartrate | 5.1 g |
| sorbitol (70%) | 7 g |
| glycerol (85%) | 7 g |
| NaOH 2M | 24 ml |
| water | 191 ml |
| titanium dioxide | 0.3 g |
| lemon oil | 2 ml |
| peppermint flavour | 1 ml |
| sodium alginate (Protanal ®LFR 5/60, sold by FMC BioPolymer) | 23.76 g |
| sodium alginate (Protanal ®LFR 10/60, sold by FMC BioPolymer) | 2.94 g |

An aqueous dispersion of titanium dioxide was prepared. Nicotine bitartrate was admixed with the dispersion and dissolved therein, and then NaOH was added. Sorbitol, glycerol, and flavours were added to the alkaline solution, followed by the sodium alginate to obtain a film-forming solution having a pH of 11.6. The solution was cast and dried to provide a dry film. From the dry film, samples were cut having a surface area of 3 cm², a thickness of 0.07 mm and weighing 35 mg. The film samples were separately packaged in aluminium/PET/PE foil envelopes and sealed, and the packaged films were stored at room temperature.

The nicotine contents of the films were determined using HPLC (High Pressure Liquide Chromatograph), by dissolving each film in 50 ml of buffer (pH 8.5) and 15% acetonitrile and using a mobile phase of 30% acetonitrile and 70% pH 8.5 buffer. A nicotine standard was used to keep track of the response rate for the system and the response was measured in mVs.

The first nicotine determination was made on a freshly made and dried film, the second was made on a film from the same batch, after 4 months of storage. Each time, three 35 mg film samples were used and the mean was calculated based on the three measurements. The determined drop of nicotine content according to the HPLC analysis was less than 5%.

Example 5

The ingredients used in Example 5 are listed in Table 8.

TABLE 8

| Ingredient | Amount |
| --- | --- |
| nicotine bitartrate | 5.1 g |
| sorbitol (70%) | 7 g |
| glycerol (85%) | 7 g |
| NaOH 2M | 15 ml |
| buffer 0.1M $Na_2CO_3$/$NaHCO_3$, 50/50 (pH 8.5) | 180 ml |
| titanium dioxide | 0.3 g |
| lemon oil | 2 ml |
| peppermint flavour | 1 ml |
| sodium alginate (Protanal ®LFR 5/60, sold by FMC BioPolymer) | 26.7 g |

A dispersion of titanium dioxide in buffer was prepared. Nicotine bitartrate was admixed with the dispersion and dissolved therein, and then NaOH was added. Sorbitol, glycerol, and flavours were added to the alkaline solution, followed by sodium alginate to obtain a film-forming solution having a pH of 10.75. The solution was cast and dried to provide a dry film.

From the dry film, samples were cut having a surface area of 3 $cm^2$, a thickness of 0.07 mm and weighing 35 mg.

The film samples were separately packaged in aluminium/PET/PE foil envelopes, which were subsequently sealed and stored at room temperature.

The first nicotine determination was made on a freshly made and dried film, the second was made on a film from the same batch, after 4 months of storage. Each time, three 35 mg film samples were used and the mean was calculated based on the three measurements. The determined drop of nicotine content according to the HPLC analysis was less than 5%.

Example 6

The ingredients used in Example 6 are listed in Table 9.

TABLE 9

| Ingredient | Amount |
| --- | --- |
| nicotine bitartrate | 5.1 g |
| sorbitol (70%) | 7 g |
| glycerol (85%) | 7 g |
| NaOH 2M | 24 ml |
| water | 171 ml |
| titanium dioxide | 0.3 g |
| lemon oil | 2 ml |
| peppermint flavour | 1 ml |
| sodium alginate (Protanal ®LFR 5/60, sold by FMC BioPolymer) | 26.7 g |

An aqueous dispersion of titanium dioxide was prepared. Nicotine bitartrate was admixed with the dispersion and dissolved therein, and then NaOH was added. Sorbitol, glycerol, and flavours were added to the alkaline solution, followed by sodium alginate to obtain a film-forming solution having a pH of 10. The solution was cast and dried to provide a dry film. From the dry film, samples were cut having a surface area of 3 $cm^2$, a thickness of 0.07 mm and weighing 35 mg.

The film samples were separately packaged in aluminium/PET/PE foil envelopes, which were subsequently sealed and stored at room temperature.

The first nicotine determination was made on a freshly made and dried film, the second was made on a film from the same batch, after 4 months of storage. Each time, three 35 mg film samples were used and the mean was calculated based on the three measurements. The determined drop of nicotine content according to the HPLC analysis was less than 5%.

Example 7

The ingredients used in Example 7 are listed in Table 10.

TABLE 10

| Ingredient | Amount |
| --- | --- |
| nicotine bitartrate | 5.1 g |
| sorbitol (70%) | 7 g |
| glycerol (85%) | 7 g |
| NaOH 2M | 25 ml |
| water | 171 ml |
| titanium dioxide | 0.3 g |
| lemon oil | 2 ml |
| peppermint flavour | 1 ml |
| sodium alginate (Protanal ®LFR 5/60, sold by FMC BioPolymer) | 26.7 g |

An aqueous dispersion of titanium dioxide was prepared. Nicotine bitartrate was admixed with the dispersion and dissolved therein, and then NaOH was added. Sorbitol, glycerol, and flavours were added to the alkaline solution, followed by sodium alginate to obtain a film-forming solution having a pH of 11. The solution was cast and dried to provide a dry film. From the dry film, samples were cut having a surface area of 3 $cm^2$, a thickness of 0.07 mm and weighing 35 mg.

The film samples were separately packaged in aluminium/PET/PE foil envelopes, which were then sealed and stored at room temperature.

The first nicotine determination was made shortly after film preparation, the second was made after 4 months of storage. Each time, three 35 mg film samples were used and the mean was calculated based on the three measurements. The determined drop of nicotine content according to the HPLC analysis was less than 5%.

Comparative Example 1

The ingredients used in Comparative Example 1 are listed in Table 9.

TABLE 11

| Ingredient | Amount |
| --- | --- |
| nicotine bitartrate | 5.1 g |
| sorbitol (70%) | 7 g |
| glycerol (85%) | 7 g |
| NaOH 2M | 22 ml |
| water | 171 ml |

TABLE 11-continued

| Ingredient | Amount |
|---|---|
| titanium dioxide | 0.3 g |
| lemon oil | 2 ml |
| peppermint flavour | 1 ml |
| sodium alginate (Protanal ®LFR 5/60, sold by FMC BioPolymer) | 26.7 g |

An aqueous dispersion of titanium dioxide was prepared. Nicotine bitartrate was admixed with the dispersion and dissolved therein, and then NaOH was added. Sorbitol, glycerol, and flavours were added to the alkaline solution, followed by sodium alginate, to obtain a film-forming solution having a pH of 9.3. The solution was cast and dried to provide a dry film. From the dry film, samples were cut having a surface area of 3 cm$^2$, a thickness of 0.07 mm and weighing 35 mg.

The film samples were separately packaged in aluminium/PET/PE foil envelopes, which were subsequently sealed and stored at room temperature.

The first nicotine determination was made shortly after film preparation, the second was made after 4 months of storage. Each time, three 35 mg film samples were used and the mean was calculated based on the three measurements. The determined drop of nicotine content according to the HPLC analysis exceeded 7%.

Comparative Example 2

The ingredients used in Comparative Example 2 are listed in Table 12.

TABLE 12

| Ingredient | Amount |
|---|---|
| nicotine bitartrate | 5.5 g |
| sorbitol (70%) | 3 g |
| glycerol (85%) | 2 g |
| buffer 0.1M K$_2$HPO$_4$/KH$_2$PO$_4$ (pH 8.5) | 80 ml |
| sodium alginate (Protanal ®LFR 5/60, sold by FMC BioPolymer) | 11 g |

Nicotine bitartrate was mixed with the buffer. Glycerol and sorbitol were added. Sodium alginate was added to the thus prepared aqueous solution at room temperature in small portions and mixed until a homogenous solution was obtained, to obtain a film forming solution having a pH of 5.5. A film prepared at such low pH would not be useful for mucosal administration of nicotine, since on dissolution in the mouth, nicotine would be present only in ionized form, not in the bioavailable free base form.

The invention claimed is:

1. A mucoadhesive nicotine-containing film, obtainable by
preparing an aqueous solution at a pH of from 9.5 to 13, by admixing:
(i) a nicotine salt,
(ii) an alkaline pH regulating agent, and
(iii) a film-forming agent comprising an alginate salt of monovalent cation or a mixture of alginate salts of monovalent cations, the film-forming agent having a mean guluronate content of from 50 to 85% by weight, a mean mannuronate content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;
distributing the solution onto a solid surface; and
permitting the solution to dry on said surface, to provide a film having a level of dryness equal to that which it would have in equilibrium with a surrounding atmosphere having a relative humidity of 10 to 40% at 25° C.

2. The film according to claim 1, wherein the pH regulating agent is LiOH, NaOH or KOH.

3. The film according to claim 2, wherein the nicotine salt is an acid addition salt.

4. The film according to claim 3, wherein the acid addition salt is a salt of tartaric acid.

5. The film according to claim 1, wherein the nicotine salt is an acid addition salt.

6. The film according to claim 5, wherein the acid addition salt is a salt of tartaric acid.

7. The film according to claim 1, comprising a plasticizer.

8. The film according to claim 1, comprising a filler.

9. The film according to claim 1, having a thickness in the range of from 0.01 mm to 2 mm.

10. The film according to claim 1, having a loss of nicotine of less than 5% by weight after 100 days in air at a temperature ranging from 21 to 24° C. and a relative humidity of 19-32%.

11. A nicotine dosage unit comprising a film according to claim 1.

12. The dosage unit according to claim 11, having a surface area in the range of from 2 to 8 cm$^2$.

13. The dosage unit according to claim 12, having a nicotine content in the range of from 0.5 mg to 4 mg.

14. The dosage unit according to claim 11, having a nicotine content in the range of from 0.5 mg to 4 mg.

15. A method of manufacturing a nicotine-containing mucoadhesive film, comprising:
preparing an aqueous solution at a pH of from 9.5 to 13, by admixing:
(i) a nicotine salt,
(ii) an alkaline pH regulating agent, and
(iii) a film-forming agent comprising an alginate salt of monovalent cation. or a mixture of alginate salts of monovalent cations, the film-forming agent having a mean guluronate content of from 50 to 85% by weight, a mean mannuronate content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;
distributing the solution onto a solid surface; and
permitting the solution to dry on said surface, to provide a film having a level of dryness equal to that which it would have in equilibrium with a surrounding atmosphere having a relative humidity of 10 to 40% at 25° C.

16. The method according to claim 15, comprising adding a plasticizer to the solution.

17. The method according to claim 15, comprising adding a filler to the solution.

18. The method according to claim 15, comprising dividing the film into dosage units.

19. A nicotine-containing film formulation for buccal administration of free base nicotine produced according to the method of claim 15, wherein the film formulation has a decrease in nicotine content of less than 5% by weight after 100 days in air at a temperature ranging from 21 to 24° C. and a relative humidity of 19-32%.

20. A method of preparing a nicotine-containing film formulation for buccal administration of free base nicotine, wherein the film formulation has a decrease in nicotine content of less than 5% by weight after 100 days in air at a temperature ranging from 21 to 24° C. and a relative humidity of 19-32%, said method comprising
  preparing an aqueous solution at a pH of from 9.5 to 13, by admixing:
  (i) a nicotine salt,
  (ii) an alkaline pH regulating agent, and
  (iii) a film-forming agent comprising an alginate salt of monovalent cation or a mixture of alginate salts of monovalent cations, the film-forming agent having a mean guluronate content of from 50 to 85% by weight, a mean mannuronate content of from 15 to 50% by weight, a mean molecular weight of from 30,000 g/mol to 90,000 g/mol and being such that a 10% aqueous solution thereof at a temperature of 20° C. has a viscosity of 100-1000 mPas, as measured at a shear rate of 20 rpm by use of a Brookfield viscometer with a spindle No. 2;
  distributing the solution onto a solid surface; and permitting the solution to dry on. said surface, to provide a film having a level of dryness equal to that which it would have in equilibrium with a surrounding atmosphere having a relative humidity of 10 to 40% at 25° C.

* * * * *